United States Patent

Fukuda et al.

Patent Number: 5,580,549
Date of Patent: Dec. 3, 1996

[54] EXTERNAL PREPARATION FOR SKIN

[75] Inventors: Minoru Fukuda; Masako Naganuma; Yuki Yamase; Yoshihiro Yokokawa; Hisayuki Komasaki, all of Yokohama, Japan

[73] Assignee: Shiseido Co., Ltd., Tokyo, Japan

[21] Appl. No.: 406,244

[22] Filed: Mar. 16, 1995

Related U.S. Application Data

[63] Continuation of Ser. No. 60,998, May 14, 1993, abandoned.

[30] Foreign Application Priority Data

May 22, 1992 [JP] Japan .................... 4-155910
May 15, 1992 [JP] Japan .................... 4-148688

[51] Int. Cl.⁶ ............................... A61K 7/135
[52] U.S. Cl. ............. 424/62; 424/401; 424/DIG. 5; 514/944
[58] Field of Search ............. 424/401, 62, DIG. 5; 514/944

[56] References Cited

U.S. PATENT DOCUMENTS

| | | | |
|---|---|---|---|
| 4,559,328 | 12/1985 | Smerbeck et al. | 424/401 |
| 4,582,865 | 4/1986 | Balazs et al. | 524/29 |
| 5,164,185 | 11/1992 | Charpin et al. | 514/159 |

FOREIGN PATENT DOCUMENTS

| | | |
|---|---|---|
| 663187 | 10/1965 | Belgium . |
| 0036534 | 9/1981 | European Pat. Off. . |
| 052233 | 12/1966 | United Kingdom . |
| 076425 | 7/1967 | United Kingdom . |
| WOA8504101 | 9/1985 | WIPO . |
| WOA9105543 | 5/1991 | WIPO . |

OTHER PUBLICATIONS

JP 63207238, Abstract 1988.
JP 4036238, Abstract 1992.
JP A 118 6811, Abstract 1989.

*Primary Examiner*—Jyothsna Venkat
*Attorney, Agent, or Firm*—Townsend & Banta

[57] ABSTRACT

An external preparing for skin comprising one or more than two types of 2-hydroxy benzoic acid derivative and/or salt thereof represented by the following formula:

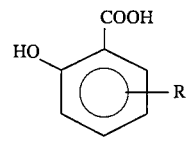

wherein R is an alkoxy group or alkyl group in the formula. The external preparation for the skin according to the present invention has a suppression effect on melanine generation by inhibition of tyrosinase activity. Accordingly, an excellent bleaching effect based upon the suppression of chromatosis and a high degree of safety can be obtained.

10 Claims, No Drawings

EXTERNAL PREPARATION FOR SKIN

This application is a file wrapper continuation of application Ser. No. 08/060,998, filed May 14, 1993, abandoned.

FIELD OF THE INVENTION

The present invention relates to an external preparation for skin and more particularly, to an improvement of bleaching ingredients thereof.

BACKGROUND ART

There are various dyschromatosis of the skin such as chloasma and ephelis in the field of dermatosis as well as spots and freckles in the field of beauty science. Since there are many obscure points in the action mechanism of dyschromatosis, it is known that abnormalities of hormones and ultraviolet rays from the sunlight causes stimulation, and melanine is formed and abnormally deposits in the skin. Melanine generation inhibitors are used for the cure of such dyschromatosis as the symptomatic therapy, e.g. an oral administration of a large amount of vitamin C, injecting glutathione, and regional application of ointment, cream or lotion including kojic acid, vitamin C and the derivative thereof or cysteine. However, an adequate bleaching effect has not been obtained by these treatments.

On the other hand, in Europe and U.S.A., hydroquinone and derivatives thereof, which are known as melanine generation inhibitors, are used for the purpose of bleaching erythema dyschromium perstans.

However, the onset of the effect was very slow when the hydroquinone derivatives were used and the bleaching effect was not enough. Although the bleaching effect was tentatively admitted in hydroquinone itself, application of the hydroquinone derivatives are limited because of safety problems. Several investigations were carried out for ingredients which could reduce the side effect of the hydroquinone and have an excellent bleaching effect, but the ingredients which have an adequate effect and are safe have not been obtained.

DISCLOSURE OF THE INVENTION

Accordingly, it is an object of the present invention to eliminate the above-described problems of the prior art and to provide an external preparation for the skin which has an excellent bleaching effect and is highly safe and stable.

As a result of studies undertaken by the present inventors so as to attain this aim, it has been found that certain types of 2-hydroxy alkoxybenzoic acid and 2-hydroxy alkylbenzoic acid have a melanine generation depressant effect and a excellent bleaching effect to improve dyspigmentation in the skin. The present invention has been achieved on the basis of this finding.

In the first aspect of the present invention, there is provided an external preparation for skin including one or more than two types of 2-hydroxy benzoic acid derivatives represented by the following general formula (A).

GENERAL FORMULA (A):

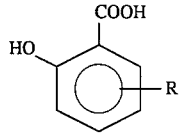

(R represents alkoxy group or alkyl group in the FORMULA (A))

In the second aspect of the present invention, there is provided an external preparation for the skin characterized in that the alkoxy group is methoxy group.

In the third aspect of the present invention, there is provided an external preparation for the skin characterized in that the alkoxy group is ethoxy group.

In the forth aspect of the present invention, there is provided an external preparation for the skin characterized in that one or more than two types of acid mucopolysaccharides are further included therein.

In the fifth aspect of the present invention, there is provided an external preparation for the skin characterized in that one or more than two types of vitamin E esters are further included therein.

In the sixth aspect of the present invention, there is provided an external preparation for the skin characterized in that one or more than two types of p-hydroxybenzoate esters are further included therein.

In the seventh aspect of the present invention, there is provided an external preparation for the skin characterized in that one or more than two types of alkylene diamine carboxylate derivatives are further included therein.

Also, it has been found that certain types of 2-hydroxy alkylbenzoic acid have a melanotic generation depressant effect and excellent bleaching effect to improve the dyspigmentation of the skin.

In the eighth aspect of the present invention, there is provided an external preparation for the skin characterized in that the alkyl group is selected from a methyl group, ethyl group, propyl group, isopropyl group, butyl group or isobutyl group.

The composition of the present invention is explained in detail hereinafter.

The 2-hydroxy alkoxybenzoic acid used for the external preparation for the skin of the present invention is a known material, e.g. 2-hydroxy-5-methoxy benzoic acid can be synthesized by the way described in Beil, 10227, and 2-hydroxy-4-methoxybenzoic acid can be synthesized by the way described in Bell, 10379. Also, these have been marketed as reagents from the ALDRICH COMPANY (GERMANY) and it is possible to use these marketed ingredients.

The 2-hydroxy alkylbenzoic acid used for the external preparation for the skin of the present invention is a also known material, e.g. 2-hydroxy-5-methylbenzoic acid can be synthesized by the way described in Bell, 10227, and 2-hydroxy-3-methylbenzoic acid can be synthesized by the way described in Bell, 10220. Furthermore, it is possible to use marketed ingredients.

The hydroxy alkoxybenzoic acid according to the present invention is a substance of which any of hydrogen atom at 3-, 4- or 5- of salicylic acid is substituted for an alkoxy group and the alkoxy group as a substituent is preferably a methoxy group, ethoxy group, propoxy group, isopropoxy group, butoxy group or isobutoxy group, and more preferably methoxy group or ethoxy group. As for example,
2-hydroxy-3-methoxybenzoic acid
2-hydroxy-3-ethoxybenzoic acid
2-hydroxy-4-methoxybenzoic acid
2-hydroxy-4-ethoxybenzoic acid
2-hydroxy-4-propoxybenzoic acid
2-hydroxy-4-isopropoxybenzoic acid
2-hydroxy-4-butoxybenzoic acid
2-hydroxy-5-methoxybenzoic acid
2-hydroxy-5-ethoxybenzoic acid 2-hydroxy-5-propoxybenzoic acid are cited.

The 2-hydroxy alkylbenzoic acid according to the present invention is a substance which any of hydrogen atom at 3-, 4- or 5- of salicylic acid is substituted for an alkyl group and the alkyl group as a substituent is preferably a methyl group, ethyl group, propyl group, isopropyl group, butyl group or isobutyl group. As for example, 2-hydroxy-3-methylbenzoic acid
2-hydroxy-3-ethylbenzoic acid
2-hydroxy-4-methylbenzoic acid
2-hydroxy-4-ethylbenzoic acid
2-hydroxy-4-propylbenzoic acid
2-hydroxy-4-isopropylbenzoic acid
2-hydroxy-4-butylbenzoic acid
2-hydroxy-5-methylbenzoic acid
2-hydroxy-5-ethylbenzoic acid
2-hydroxy-5-propylbenzoic acid
are cited.

The 2-hydroxy alkoxybenzoic acid can be easily exchanged in the form of salt, and the 2-hydroxy alkoxybenzoic acid in the form of salt can be added to the external preparation for the skin of the present invention. Although the salt is not limited, but as for example of the salt, salt with alkali metal or alkaline earth metal such as sodium salt, potassium salt and calcium salt, ammonium salt or amino acid salt be cited.

The 2-hydroxy alkylbenzoic acid can be easily exchanged in a form of salt, and the 2-hydroxy alkylbenzoic acid in the form of salt can be added to the external preparation for the skin of the present invention. Although the salt is not limited, but as for a example of the salt, salt with alkali metal or alkaline earth metal such as sodium salt, potassium salt and calcium salt, ammonium salt or amino acid salt can be cited.

Although the 2-hydroxy alkoxybenzoic acid is known material in the prior art, the bleaching effect of the above 2-hydroxy alkoxybenzoic acid has not been known. The inventors originally discovered the bleaching effect and added the 2-hydroxy alkoxybenzoic acid to the external preparation for the skin for the purpose of obtaining a bleaching effect.

The content of the 2-hydroxy alkoxybenzoic acid and/or the salt is preferably 0.001 to 20 weight %, and more preferably 0.01–10 weight % to the total amount of the external preparation for the skin.

If the content is less than 0.001 weight %, the bleaching effect might not be enough, and if the content becomes more than 20 weight %, the further improvement of the bleaching effect might not be obtained.

Also, if acid mucopolysaccharides, vitamin E esters, p-hydroxybenzoate esters or alkylene diamine carboxylate derivative are added to the external preparation for the skin, the bleaching effect can be extremely improved. These ingredients are well known as moisturing ingredients, hematogenic ingredients, preservatives and bactericides, and have been added in external preparations for the skin such as cosmetics, but the improvement of bleaching effect has not been known.

As an example of the acid mucopolysaccharides used in the present invention, a sodium hyaluronate and sodium chondroitin sulfate are cited. The content of the acid mucopolysaccharides is preferably 0.01–10 weight % and more preferably 0.01 to 3 weight % in the total amount of the external preparation for the skin.

As an example of the vitamin E ester, α-tocopherol, β-tocopherol, γ-tocopherol, δ-tocopherol, tocopherol acetate, and tocopherol nicotinate are cited.

As an example of the p-hydroxybenzoate, methyl p-hydroxybenzoate, ethyl p-hydroxybenzoate, butyl p-hydroxybenzoate etc. can be cited.

As an example of alkylenediamine carboxylate derivatives, ethylenediamine tetra acetic acid and salt thereof can be cited. The alkylenediamine carboxylate derivatives include alkali metal salt or alkaline earth metal such as sodium salt, potassium salt and magnesium salt, ammonium salt and alkanol salt and the sodium salt is most preferable.

The content of the vitamin E ester, p-hydroxybenzoate and/or alkylene diamine carboxylic acid derivative is preferably 0.01 to 3 weight % and more preferably 0.05 to 0.3 weight % in the total amount of the external preparation, respectively.

Although the 2-hydroxy alkylbenzoic acid and salt thereof are also known in the prior art, the bleaching effect of the above 2-hydroxy alkylbenzoic acid has not been known. The inventor originally discovered the bleaching effect and added the 2-hydroxy alkylbenzoic acid to the external preparation for the skin for the purpose of obtaining the bleaching effect.

The content of the 2-hydroxy alkyl benzoic acid is preferably 0.001 to 20 weight %, and more preferably 0.01 to 10 weight % in the total amount of the external preparation for the skin.

If the content is less than 0.001 weight %, the bleaching effect might not be enough, and if the content becomes more than 20 weight %, farther improvement of the bleaching effect might not be obtained It is possible to select any form of the external preparation for the skin, e.g. a solubilized system such as lotion or liquid, an emulsified system such as milky lotion or cream, a dispersed system such as make-up cosmetics, pack, jelly or ointment.

It is also possible to add other ingredients which can be used for the ordinal cosmetics or medicine into the external preparation for skin according to the present invention. As an example of the other ingredients, other bleaching ingredients, moisturing ingredients, antioxidants, oily ingredients, ultraviolet absorbents, surfactants, thickener, alcohol, powder, dye, water soluble ingredients, water, nutritive ingredients an skin are cited.

As an example of the oily ingredient:

natural fat and oil such as camellia oil, macadamia nuts oil, olive oil, castor oil, safflower oil, soybean oil, tea fruit oil, cacao oil, coconut oil, hardened coconut oil, palm oil, japan wax, hydrogenated castor oil, yellow bees wax, candelilla wax, carnauba wax, lanolin, liquid lanolin, jojoba wax, hard lanolin, polyoxyethylene lanolin alcohol ether, polyoxyethylene cholesterol ether;

hydrocarbon fat add oil such as liquid paraffin, ozokerite, squalene, paraffin, ceresin, vaseline, microcrystalline wax;

synthesized oil such as isopropyl myristate, octyldodecyl myristate, isopropyl palmitate, cholesteryl 12-hydroxystearate, ethylene glycol di-2-ethyl hexylate, dipentaerythritol fatty acid ester, pentaerythritol tetra-2-ethyl hexylate, glycerol tri-2-ethyl hexylate, tri-isosteatate tri-methylol propane, cetyl-2-ethyl hexanoate, methyl ricinoleate;

chain polysiloxane such as dimethyl polysiloxane, methyl phenyl polysiloxane, methyl hydrogen polysiloxane;

cyclic polysiloxane such as decamethyl polysiloxane, dodecamethyl polysiloxane, tetramethyl tetrahydrogen polysiloxane;

silicones such as silicone resin which can a form three dimensional network structure and silicon rubber are cited.

As an example of the ultraviolet absorbents.

benzoic acid derivatives such as p-aminobenzoic acid, monoglyceryl p-aminobenzoate, ethyl N,N-dipropoxy p-aminobenzoate, ethyl N,N-dimethyl p-aminobenzoate;

anthranilate derivatives such as homomenthyl-N-acetyl anthranilate;

salicylate derivatives such as amyl salicylate, homomenthyl salicylate, octyl salicylate, phenyl salicylate, benzyl salicylate, p-isopropanol phenyl salicylate;

cinnamate derivatives such as octyl cinnamate, ethyl-4-isopropyl cinnamate, methyl-2,5-diisopropyl cinnamate, ethyl-2,4-diisopropyl cinnamate, propyl p-methoxy cinnamate, iso-amyl p-methoxy cinnamate, octyl p-methoxy cinnamate (2-ethyl hexyl-p-methoxy cinnamate), 2-ethoxy ethyl-p-methoxy cinnamate, 2-ethyl hexyl-α-cyano-β-phenyl cinnamate, glyceryl mono-2-ethyl hexanoyl-di-p-methoxy cinnamate;

benzophenone derivatives such as 2,4-dihydroxy benzophenone, 2,2'-dihydroxy-4-methoxybenzophenone, 2,2',4,4'-tetrahydroxybenzophenone, 2-hydroxy-4-methoxybenzophenone, 2-hydroxy-4-methoxybenzophenone-5-sulfonate, 4-phenylbenzophenone, 2-ethylhexyl-4'-phenylbenzophenone-2-carboxylate;

and other ultraviolet absorbents such as 3-(4'-methyl benzylidene)-d,1-camphor, 3 benzylidene-d,1-camphor, urocanic acid, ethyl urocanate, 2,2'-hydroxy-5-methyl phenyl benzotriazole, 2-(2'-hydroxy-5'-t-octylphenyl) benzotriazole, dibenzaladine, dianisoilmethan, 4-methoxy-4'-t-butyl dibenzoylmethane, 5-(3,3-dimethyl norbornyliden)-3-pentane-2-on are cited.

As an example of lipophilic nonionic surfactants;

sorbitan fatty acid ester such as sorbitan monooleate, sorbitan monoisostearate, sorbitan monolaurate, sorbitan monopalmitate, sorbitan monostearate, sorbitan sesquioleate, diglycerol sorbitan penta-2-ethyl hexylate;

esters of glycerol or polyglycerine such as glyceryl monostearate, glyceryl-α,α'-oleate pyroglutamate, glyceryl monostearate malate;

propylene glycol fatty acid ester such as propylene glycol monostearate;

and other nonionic surfactants such as hydrogenated castor oil derivative, glycerol alkyl ether are cited, As an example of hydrophilic nonionic surfactant;

polyoxyethylene sorbitan fatty acid ester such as polyoxyethylene sorbitan monooleate, polyoxyethylene sorbitan monostearate;

polyoxyethylene sorbitol fatty acid ester such as polyoxyethylene sorbitol monolaurate, polyoxyethylene sorbitol mono oleate, polyoxyethylene sorbitol mono stearate;

polyoxyethylene glycerin fatty acid ester such as polyoxyethylene glycerin monostearate, polyoxyethylene glycerin monoisostearate, polyoxyethylene glycerin triisostearate;

polyoxyethylene fatty acid ester such as polyoxyethylene monooleate, polyoxyethylene distearate;

polyoxyethylene alkyl ether such as polyoxyethylene lauryl ether, polyoxyethylene oleyl ether, polyoxyethylene stearyl ether, polyoxyethylene-2-octyl dodecyl ether, polyoxyethylene cholestanol ether;

polyoxyethylene alkyl phenyl ether such as polyoxyethylene octyl phenyl ether, polyoxyethylene nonyl ether, polyoxyethylene dinonylphenyl ether;

pluronic type surfactants such as PLURONIC™;

polyoxyethylene polyoxypropylene alkyl ether such as polyoxyethylene polyoxypropylene cetyl ether, polyoxyethylene polyoxypropylene-2-decyl tetradecyl ether, polyoxyethylene polyoxypropylene monobutyl ether, polyoxyethylene polyoxypropylene, hydrogenated lanolin, polyoxyethylene polyoxypropylene glycerin ether;

condensed tetra polyoxyethylene tetra polyoxypropylene ethylene diamine such as tetronic;

polyoxyethylene castor oil derivatives or polyoxyethylene hydrogenated castor oil derivatives such as polyoxyethylene castor oil, polyoxyethylene hydrogenated castor oil, polyoxyethylene hydrogenated castor oil monoisostearate, polyoxyethylene hydrogenated castor oil tri-isostearate, polyoxyethylene hydrogenated castor oil mono pyroglutamate mono-isostearate diester, polyoxyethylene hydrogenated castor oil maloate ester;

alkanolamide such as coconut fatty acid diethanolamide, lauric acid monoethanolamide, fatty acid isopropanol amide, and other nonionic surfactants such as polyoxyethylene propylene glycol fatty acid ester, polyoxyethylene alkyl amine, polyoxyethylene fatty acid amide, sucrose fatty acid ester, condensed polyoxyethylene nonyl phenyl formaldehyde, alkyl ethoxy dimethyl amine oxide, trioleyl phosphate are cited.

As an example of anion surfactant:

fatty acid soap such as sodium laurate, sodium palmitate;

higher alkyl sulfate ester salt such as sodium lauryl sulfate, potassium lauryl sulfate;

alkyl ether sulfate ester salt such as polyoxyethylene lauryl sulfate triethanolamine, polyoxyethylene sodium lauryl sulfate;

N-acyl sarcosine acid such as sodium lauroyl sarcosine:

higher fatty acid amide sulfate such as sodium N-myristoyl-N-methyl taurine, sodium coconuts oil fatty acid methyl tauride, sodium lauryl methyl tauride;

phosphate ester salt such as sodium polyoxyethylene oleyl ether phosphate, sodium polyoxyethylene stearyl ether phosphate;

sulfosuccinate such as sodium di-2-ethylhexyl sulfosuccinate, sodium monolauroylmonoethanolamide polyoxyethylene sulfosuccinate, sodium laurylpolypropylene glycol sulfosuccinate;

alkylbenzensufonate such as sodium linear dodecylbenzen sulfonate, triethanolamine lineardodecylbenzen sulfonate;

N-acylglutamic acid such as monosodium N-lauroylglutamate, disodium N-stearoyl glutamate;

higher fatty acid ester sulfonate ester salt such as sodium hydrogenated glyceryl cocoate sulfate;

polyoxyethylene alkyl ether carboxylate, α-olefin sulfonate, higher fatty acid ester sulfonate. secondary alcohol sulfate salt, higher fatty acid alkyrolamide sulfate salt, sodium lauroyl monoethanolamide succinate, N-palmitoyl aspartic acid, di-triethanol amine, alkali salt of coco-hydrolyzed collagen are cited.

As an example of cationic surfactants;

salt of alkyltrimethylammonium such as stearyl trimethyl ammonium chloride, lauryl trimethyl ammonium chloride:

salt of dialkyl dimethyl ammonium such as distearyl dimethyl ammonium chloride;

alkyl pyridinium salt such as poly (N,N'-dimethyl-3,5-methylene piperidinium) chloride, cetyl pyridinium chloride:

other cationic surfactants such as alkyl tetra ammonium salt, alkyl dimethyl benzyl ammonium salt, alkyl isoquinolimium salt, dialkyl dimorphonium salt, polyoxyethylene alkylamine, alkylamine salt, polyamine fatty acid derivative, amylalcohol fatty acid derivative, benzalkonium chloride, benzethonium chloride, cation polymer, acrylic acid β-N,N-dimethyl-N-ethylammonioethyl vinyl chloride pyrolidone copolymer are cited.

As an example of ampholytic surfactants, imidazoline derivatives such as sodium 2-undecyl-N,N,N-hydroxyethyl calboxymethyl)-2-imidazoline, disodium 2-cocoil-2imidazolinium hydroxyde-1-calboxyethyloxy;

betaine derivatives such as 2-heptadecyl-N-calboxymethyl-N-hydroxyethylimidazolinium betaine, lauryldimethylamino acetate betaine, alkyl betaine, amide betaine, sulfo betaine are cited.

As for example of moisturing ingredients, such as cholesteril-12-hydroxystearate, sodium lactate, dl-pyrolidone carboxylate, urea, adduct of diglycerine ethylene oxide and propylene oxide, and if the acid mucopolysaccharides such as chondroitin sulfate or hyaluronic acid are added to the external preparation for the skin, it is possible to improve the bleaching effect of the hydroxy alkoxybenzoic acid.

As an example of thickener, arabian gum, carageenan, tragacanth gum, quince seed, casein, sodium casein, dextrin, gelatin, sodium alginate, methyl cellulose, ethyl cellulose, carboxymethylcellulose, hydroxyethyl cellulose, hydroxypropylcellulose, polyvinyl alcohol, sodium polyacrylate, carboxyvinyl polymer, cyamoposis gum, xanthan gum, magnesium aluminum silicate, bentonite, hectolight are cited.

As an example of polyhydric alcohol, ethylene glycol, propylene glycol, dipropylene glycol, 1,3-butylene glycol, glycerol, erythritol, trimethylol-propane, pentaerythritol, sorbitol, maltitol, diglycerine, and polyethylene glycol are cited.

As an example of higher alcohol, lauryl alcohol, stearyl alcohol, behenyl alcohol, myrystyl alcohol, oleyl alcohol, cetostearyl alcohol, monostearyl glycerin ether (batyl alcohol), lanolin alcohol, cholesterol, phytosterol, isostearyl alcohol, and octytdodecanol are cited.

As an example of powder.

inorganic powder such as talc, kaolin, mica, sericite, phlogopite, synthetic mica, magnesium carbonate, calcium carbonate, aluminum silicate, silica, zeolite, barium sulfate, baked calcium sulfate (burned gypsum), calcium phosphate, fluoric apatite, hydroxyapatite, ceramic powder, metallic soap (myristic acid zinc, calcium palmitate, aluminum stearate), boron nitride;

organic powder such as polyamide resin powder (nylon powder), polyethylene powder, poly-methyl methacrylate powder, polystyrene powder, copolymer resin powder of styrene and acrylic acid, polymethycyl sesquioxane powder, cellulose powder;

inorganic pigment such as titanium dioxide, zinc oxide, iron oxide (the red ocher), iron titanate, yellow iron oxide, black iron oxide, carbon black, lower titanium oxide, manganese violet, cobalt violet, chromium oxide, ultramarine, iron blue;

pearl pigment such as titanium oxide coated mica, titanium oxide coated oxybismuth chloride, colored titanium oxide coated mica, bismuth oxychloride, scale foil;

metallic powder pigment such as aluminum powder;

organic pigment such as Red #201, Red #202, Orange #203, Yellow #205, Yellow #401, Blue #404, organic pigment such as zirconium, barium or aluminum lake of Red #3, Yellow #4, Green #3, Blue #1, natural color pigments such as chlorophyll, β-catoten are cited.

As an example of synthetic resin emulsion, acrylic resin emulsion and poly vinyl acetate resin emulsion are cited.

As for an example of amino acid, glycine, leucine, phenylalanine, thyrosin, aspartic acid, glutamic acid, arginine, histidine, lysine, cysine, cysteine, acyl sarcosine sodium (lauroyl sarcosine sodium), acyl glutamate, glutathione, pyrolidone carboxylate are cited.

As an example of organic amine, monoethanolamine, diethanolamine, triethanolamine, morpholine, tri isopropanol amine, 2-amino 2-methyl-1,3-propanediol, 2-amino-2-methyl-1-propanol are cited.

Further, sequestering agents such as disodium edetate, trisodium edetate, sodium citrate, sodium polyphosphate, sodium metaphosphate, gluconic acid;

medicinal ingredients such as caffeine, tannin, tranexamic acid and derivatives thereof, licorice extractive (glabridin), pyracantha fortuneana, various herbal medicine, tocopherol acetate, glycyrrhizic acid and derivatives or salt thereof:

other bleaching ingredients such as Vitamin C, manganese ascorbate phosphate, glucoside ascorbate, arbutin, kojic acid;

sugars such as glucose, fructose, mannose, trehalose are cited.

It is possible to improve the bleaching effect of the hydroxy alkoxybenzoic acid and/or the salt thereof if the vitamin E ester such as tocopherol acetate are added to the external preparation for the skin of the present invention.

[EMBODIMENTS]

The composition of the present invention is explained in detail by the following example. It should be noted that the present invention isn't limited by these examples.

The examination methods which are carried out in these examples are explained before the description of the examples.

(1) EXAMINATION FOR INHIBITION OF TYROSINASE ACTIVITY

Preparation of reagents
1) L-DOPA solution
   10 mg L-DOPA (guaranteed reagent) is dissolved at the time of examination in 20 ml of phosphate buffer described in 3) below and prepared 0.05% L-DOPA solution.
2) Tyrosinase solution
   11.7 mg of mushroom tyrosinase (50,000 units/11.7 mg protein SIGMA CORPORATION) is dissolved in 25 ml of distilled water and prepared 2,000 unit/ml solution.
3) 0.1-M phosphate buffer
   The buffer was prepared at pH 8.8.

Preparation of sample solution
   The sample described in TABLE 1 below are diluted by ethanol to the concentration with 3 standards.

Examination method
   The measurement of the tyrosinase activity was carried out by a modified method of Pomerantz, using L-DOPA (guaranteed reagent) as the substrate and measuring the absorbance at 475 nm at which the absorption of dihydroxyphenylalanine chrome (reaction product) exists.

Namely, 1.0 ml of the L-DOPA solution and 1.8 ml of the phosphate buffer were added in 0.1 ml of the sample solutions. 0.1 ml of tyrosinase solution was added and mixed for reaction for 1.5 minutes at room temperature. The absorbance at 475 nm was measured by using a spectrophotometer (type 220 A Spectrophotometer, HITACHI corporation) and the measured value was expressed by T.

Also, 1.0 ml of distilled water instead of the L-DOPA solution. 1.8 ml of the phosphate buffers and 0.1 ml of the sample solutions were mixed, operated in the same way above, measured the absorbance and obtained the value T' as a reagent blank of the sample.

0.1 ml of ethanol instead of the sample solutions was added to the mixture of 1.0 mo of the L-DOPA and 1.8 ml of phosphate buffers, operated in the same way above and obtained the value C as a control.

1.8 ml of phosphate buffers and 0.1 ml of ethanol were added to 1.0 ml of distilled water instead of L-DOPA solution, operated in the same way above and obtained the value C' as a reagent blank of the control.

Inhibition of tyrosinase activity in each sample concentration were obtained by the following formula. The result was described as semilog graph of which a logarithmic scale indicates concentration of the sample and another scale indicates inhibition ratio of the activity. An inhibition concentration of which 50% of activity of the tyrosinase is suppressed (ID 50) was obtained from the graph.

Incidentally, the values T, T', C, and C' were measured three times and averages were used for the calculation.

Inhibition of tyrosinase activity $(\%) = 100 \times [1-(T-T')/(C-C')]$

(2) EXAMINATION FOR BLEACHING EFFECT

[Preparation of sample]

Lotions were prepared by the following formula, using each sample. Namely, the alcohol phase and aqueous phase according to the following formula were prepared respectively, and both phases were mixed and dissolved according to an ordinal method.

| (Alcohol phase) | |
|---|---|
| 95% Ethanol | 55.0 wt % |
| Polyoxyethylene (25 moles) hydrogenated castor oil | 2.0 |
| Sample | 1.0 |
| (Aqueous phase) | |
| Dipropylene glycol | 5.0 |
| Sodium hexametaphosphorate | q.s. |
| Ion exchanged water | balance |

[Examination method]

10 subjects for each group were exposed to sunlight in summer for 4 hours (2 hours×2 days). The lotion was applied to the facial skin of medialis brachii once each morning and evening for 5 days after the day exposed to the sunlight for 8 weeks. After the application period, depression effect to the chromatosis which was caused by the ultraviolet irradiation was examined and evaluated, the degree of which was based on The following standard.

⊙: The number of the subjects who judged the result was "extremely effective" or "effective" were equal to or more than eight (Equal to or more than 80%).

○: The number of the subjects who judged the result was "extremely effective" or "effective" were five to seven (from 50% less than 70%)

△: The number of the subjects who judged the result was "extremely effective" or "effective" were three to four (from 30% less than 40%)

×: The number of the subjects who judged the result was "extremely effective" or "effective" were less than two (less than 20%)

EXAMPLE 1 TO 8 AND COMPARISON a TO d (EFFECT OF INHIBITION OF TYROSINASE AND BLEACHING EFFECT)

The inhibition effect to the tyrosinase activity which is essential for producing the melanine and bleaching effect for human skin by the 2-hydroxy alkoxybenzoic acid were examined by using samples described in TABLE 1.

As is clear from the result, the 2-hydroxy alkoxybenzoic acid of the present invention could inhibit the activity of tyrosinase and especially the 2-hydroxy-4-methoxybenzoic acid and 2-hydroxy-5-methoxybenzoic acid could inhibit the activity at the low concentration with 1.0 mM and 4.5 mM.

On the other hand, from the bleaching effect examination, the subjects who judged the effect was "extremely effective" or "effective" were equal to or more than 80% with respect to the example 1 to 4. It is obvious that these examples had excellent bleaching effect compared with the comparative example a to d. Although the ascorbic acid according to the example c had high inhibition effect to the activity of tyrosinase, it is difficult to be absorbed into skin because of water solubility and the result of bleaching effect was rather low level.

Also, it is known that the hydroquinone according to the comparative example a and gentisic acid according to the comparative example b have side effect. However, any abnormality of skin such as erythema, eczema, clapping and so on could not be observed in the 2-hydroxy alkoxybenzoic acid according to the EXAMPLE 1 to 4.

Since detailed data is omitted, other 2-hydroxy alkoxybenzoic acid and salt thereof had also tyrosinase inhibition effect and excellent bleaching effect, and high safety. For example, 80% of the subjects indicated that a lotion including potassium 2-hydroxy-4-methoxybenzoate was effective for bleaching examination.

As described above, it is understood the 2-hydroxy alkoxybenzoic acid and/or salt of the present invention could inhibit the activity of tyrosinase and improve the chromatosis and had high bleaching effect, and high safety.

TABLE 1

| Exm. No. | Sample | ID50(mM)/bleaching effect/stability | | |
|---|---|---|---|---|
| 1 | 2-hydroxy-3-methoxybenzoic acid | 21.0 | ⊙ | ○ |
| 2 | 2-hydroxy-4-methoxybenzoic acid | 1.0 | ⊙ | ○ |

TABLE 1-continued

| Exm. No. | Sample | ID50(mM)/bleaching effect/stability | | |
|---|---|---|---|---|
| 3 | 2-hydroxy-5-methoxybenzoic acid | 4.5 | ⊙ | o |
| 4 | 2-hydroxy-4-ethoxybenzoic acid | 2.0 | ⊙ | o |
| a | hydroquinone | 4.2 | Δ | x |
| b | gentisic acid | 13.6 | Δ | Δ |
| c | ascorbic acid | 0.3 | o | o |
| d | none | — | x | — |

A same examination as described above was carried our for 2-hydroxy alkylbenzoic acid and the salt thereof, and it was found that the hydroxy alkylbenzoic acid had an inhibition effect of tyrosinase and excellent bleaching effect. The several results of the examination bleaching effect were shown in TABLE 2.

As described above, it is understood the 2-hydroxy alkylbenzoic acid and/or salt of the present invention could inhibit the activity of tyrosinase and improve the chromatosis and had high bleaching effect, and high safety.

TABLE 2

| Exm. No. | Sample | bleaching effect/stability | |
|---|---|---|---|
| 5 | 2-hydroxy-3-methylbenzoic acid | ⊙ | o |
| 6 | 2-hydroxy-4-methylbenzoic acid | ⊙ | o |
| 7 | 2-hydroxy-5-methylbenzoic acid | ⊙ | o |
| 8 | 2-hydroxy-4-ethylbenzoic acid | ⊙ | o |
| a | hydroquinone | Δ | x |
| b | gentisic acid | Δ | Δ | methoxybenzoic acid, the bleaching effect was extremely improved. However, in the case of adding the sodium hyaluronate more than 10 %, the physical properties became too sticky, and handling suitability was also bad. Accordingly, the concentration of the sodium hyaluronate is preferably 0.01 to 10.0 weight % and more preferably 0.01 to 3 weight % in the total amount of the external preparation for the skin.

Also, the improvement of bleaching effect of 2-hydroxy alkoxybenzoic acid was observed in the case of adding the sodium hyaluronate to the external preparation for the skin including other 2-hydroxy alkoxybenzoic acid and the salt. Furthermore, the improvement was observed in other acid mucopolysaccharides.

TABLE 3

| SAMPLE | Concentration in the sample lotion (Weight %) | | | | | |
|---|---|---|---|---|---|---|
| | COMP. e | EXM. 9 | EXM. 10 | EXM. 11 | EXM. 12 | EXM. 13 |
| 2-hydroxy-3-methoxybenzoic acid | 0.5 | 0.5 | 0.5 | 0.5 | 0.5 | 0.5 |
| Sodium hyaluronate | 0.0 | 0.01 | 0.1 | 0.5 | 3.0 | 10.0 |
| Bleaching effect | o | ⊙ | ⊙ | ⊙ | ⊙ | ⊙ |
| physical properties and use-ability | ⊙ | ⊙ | ⊙ | ⊙ | o | x |

EXAMPLE 9 TO 17 AND COMPARISON e
(IMPROVEMENT OF BLEACHING EFFECT)

The investigation for improvement of bleaching effect by adding other ingredients were carried out as described below.

Namely, the 2-hydroxy-3-methoxybenzoic acid as the 2-hydroxy alkoxy benzoic acid and sodium hyaluronate as the acid mucopolysaccharide were used for the examination of improvement of bleaching effect.

Lotions for the examination were prepared by adding 0.5 weight % of 2-hydroxy-3-methoxybenzoic acid into the alcohol phase and sodium hyaluronate into the aqueous phase of which the concentration as to be shown in TABLE 3.

As is clear from the TABLE 3, when 0.01% or more than 0.01% of the sodium hyaluronate was added to the external preparation for the skin including 0,5% of 2-hydroxy-3-

Further, as is clear from the examples 14 to 17 shown in the TABLE 4, tocopherol acetate, methyl p-hydroxybenzoate, ethyl p-hydroxybenzoate and disodium ethylenediamine tetraacetate had excellent improvement effect of bleaching.

Although, 2-hydroxy-3-methoxybenzoic acid was examined in the examples 14 to 17, other 2-hydroxy alkoxybenzoic acid and salts thereof had excellent improvement effect of bleaching.

Other vitamin E ester, p-amino benzoate and alkylenediamine carboxylic acid derivatives also had the improvement effect of bleaching.

The content of the vitamin E ester, p-aminobenzoic acid ester and/or alkylene diamine carboxylic acid derivative is preferably 0.01 to 3 weight % and more preferably 0.05 to 0.3 weight % in the total amount of external preparation for the skin. If the content is less than 0.01 weight %, the improving effect is not enough, and the content is more than 3 %, tile bleaching effect can not be improved any more.

TABLE 4

| SAMPLE | Concentration in the sample lotion (Weight %) | | | | |
|---|---|---|---|---|---|
| | COMP. e | EXM. 14 | EXM. 15 | EXM. 16 | EXM. 17 |
| 2-hydroxy-3-methoxybenzoic acid | 0.5 | 0.5 | 0.5 | 0.5 | 0.5 |
| tocopherol acetate | 0.0 | 0.5 | 0.0 | 0.0 | 0.0 |
| methyl p-hydroxybenzoate | 0.0 | 0.0 | 0.5 | 0.0 | 0.0 |
| ethyl p-hydroxybenzoate | 0.0 | 0.0 | 0.0 | 0.5 | 0.0 |
| disodium ethylene diamine tetra acetate | 0.0 | 0.0 | 0.0 | 0.0 | 0.5 |
| Bleaching effect | o | ⊙ | ⊙ | ⊙ | ⊙ |

The external preparation for skin according to the example 14 to 28 were prepared and examined the bleaching effect as described example 1 to 8. The bleaching effect was observed in any of the external preparation for the skin and harmful side effects were not observed, and this showed high safety of the external preparation for the skin.

Incidentally, all concentration is expressed by weight % in she following examples.

EXAMPLE 18 CREAM

The cream was prepared by the following formula. Namely, propylene glycol, potassium hydroxide and tetrasodium ethylenediamine tetra acetate were added to the ion exchanged water and kept at 70° C. (Aqueous phase). The other ingredients are mixed and dissolved at 70° C. (Oil phase). The oil phase was added to the aqueous phase gradually and preemulsified at 70° C., then uniformly emulsified with a homo mixer and then cooled down to 30° C. under stirring condition,

| | |
|---|---|
| Stearic acid | 6.0 |
| Cetostearyl alcohol | 3.0 |
| Isopropyl myristate | 18.0 |
| Glycerine monostearate | 3.0 |
| Propylene glycol | 10.0 |
| 2-hydroxy-4-butoxybenzoic acid | 15.0 |
| Potassium hydroxide | 0.2 |
| Tetrasodium ethylenediamine tetraacetate | 0.01 |
| Tocopherol acetate | 0.1 |
| Butyl p-hydroxybenzoate | q.s. |
| Perfume | q.s. |
| Ion exchanged water | balance |

EXAMPLE 19 CREAM

The cream was prepared by the following formula. Namely, propylene glycol and disodium ethylenediamine tetraacetate were added to the ion exchanged water and kept at 70° C. (Aqueous phase) The other ingredients were mixed and dissolved at 70° C. (Oil phase). The oil phase was added to the aqueous phase gradually and preemulsified at 70° C., then uniformly emulsified with a homomixer and cooled down to 30° C. under stirring condition.

| | |
|---|---|
| Stearic acid | 5.0 |
| Sorbitan monostearate | 2.5 |
| Polyoxyethylene (20) sorbitan monostearate | 1.5 |
| Propylene glycol | 10.0 |
| 2-hydroxy-3-isobutoxybenzoic acid | 4.0 |
| Glycerin trioctanoate | 10.0 |
| Squalene | 5.0 |
| Octyl p-dimethylaminobenzoate | 3.0 |
| Disodium ethylenediamine tetraacetate | 0.01 |
| Ethyl p-hydroxybenzoate | 0.3 |
| Perfume | q.s. |
| Ion exchanged water | balance |

EXAMPLE 20 CREAM

The cream was prepared by the following formula according to the same method as described in EXAMPLE 19.

| | |
|---|---|
| Stearyl alcohol | 7.5 |
| Stearic acid | 1.5 |
| Hydrogenated lanolin | 2.0 |
| Squalene | 5.0 |
| 2-Octadodecyl alcohol | 6.0 |
| Polyoxyethylene (25) cetyl ether | 3.0 |
| Glycerin monostearate | 2.0 |
| Propylene glycol | 5.0 |
| Sodium hyaluronate | 0.1 |
| Octyl cinnamate | 4.0 |
| 2-hydroxy-4-methoxybenzoic acid | 3.0 |
| Disodium ethylenediamine tetraacetate | 0.03 |
| Ethyl p-hydroxybenzoate | 0.3 |
| Perfume | q.s. |
| Ion exchanged water | balance |

EXAMPLE 21 CREAM

The cream was prepared by the following formula according to the same method as described in EXAMPLE 19.

| | |
|---|---|
| Stearic acid | 6.5 |
| Sorbitan monostearate | 2.0 |
| Polyoxyethylene (20) sorbitan monostearate | 1.5 |
| Propylene glycol | 10.0 |
| 2-hydroxy-5-ethoxybenzoic acid | 8.5 |
| Glycerin trioctanoate | 10.0 |
| Squalane | 5.0 |
| Sodium hyaluronate | 1.0 |
| Trisodium ethylenediamine tetraacetate | 0.01 |
| Glucose | 0.5 |
| Ethyl p-hydroxybenzoate | 0.3 |
| Perfume | q.s. |
| Ion exchanged water | balance |

EXAMPLE 22 CREAM

The cream was prepared by the following formula according to the same method as described in EXAMPLE 19.

| | |
|---|---|
| Stearyl alcohol | 5.5 |
| Stearic acid | 2.5 |
| Hydrogenated lanolin | 2.0 |
| Squalane | 5.0 |
| 2-Octyl dodecylalcohol | 6.0 |
| Polyoxyethylene (25) cetyl ether | 3.0 |
| Glycerin monostearate | 2.0 |

| Propylene glycol | 5.0 |
| --- | --- |
| 2-hydroxy-5-methoxybenzoic acid | 4.0 |
| Glycerin | 5.0 |
| Sodium bisulfite | 0.3 |
| Ethyl p-hydroxybenzoate | 0.3 |
| Perfume | q.s. |
| Ion exchanged water | balance |

EXAMPLE 23 CREAM

The cream was prepared by the following formula according to the same method as described in EXAMPLE 19.

| Stearyl alcohol | 5.0 |
| --- | --- |
| Stearic acid | 2.5 |
| Hydrogenated lanolin | 2.5 |
| Squalane | 5.0 |
| 2-Octyl dodecylalcohol | 6.0 |
| Polyoxyethylene (25) cetyl ether | 3.0 |
| Glycerin monostearate ester | 2.0 |
| Propylene glycol | 7.0 |
| Sodium L-ascorbate | 0.5 |
| 2-hydorxy-3-methoxy benzoate | 0.8 |
| Sodium bisulfite | 0.03 |
| Ethyl p-hydroxybenzoate | 0.3 |
| Perfume | q.s. |
| Ion exchanged water | balance |

EXAMPLE 24 CREAM

The cream was prepared by the following formula according to the same method as described in EXAMPLE 19.

| Stearyl alcohol | 6.0 |
| --- | --- |
| Stearic acid | 3.0 |
| Hydrogenated lanolin | 2.0 |
| Squalane | 5.0 |
| 2-Octyl dodecylalcohol | 6.0 |
| Polyoxyethylene (25) cetyl | 3.0 |
| Glycerin monostearate ester | 2.0 |
| Propylene glycol | 7.0 |
| 2-hydroxy-5-propoxybenzic acid | 0.05 |
| Vitamin A palmitate | 0.3 |
| Sodium bisulfite | 0.03 |
| Ethyl p-hydroxybenzoate | 0.3 |
| Perfume | q.s. |
| Ion exchanged water | balance |

EXAMPLE 25 MILKY LOTION

The milky lotion was prepared by the following formula. Namely, the carboxyvinyl polymer was dissolved in a part of the ion exchanged water (A phase). The polyethylene glycol 1500, the triethanolamine and the sodium bisulfite were added to the other part of the ion exchanged water and dissolved at 70° C. (Water phase). The other ingredients were dissolved under heating condition at 70° C. (Oil phase). The oil phase was added to the aqueous phase, and preemulsified. The A phase was added to the system and emulsified uniformly with the Homo mixer and cooled down to 30° C. under stirring condition.

| Stearic acid | 2.0 |
| --- | --- |
| Cetyl alcohol | 1.5 |
| Vaseline | 5.0 |
| Liquid paraffin | 10.0 |
| Polyoxyethylene (10) monooleate | 2.0 |
| Polyethylene glycol 1500 | 3.0 |
| Triethanolamine | 1.0 |
| Sodium hyaluronate | 0.05 |
| 2-hydroxy-4-methoxybenzoic acid | 2.0 |
| Carboxyvinyl polymer (CARBOPOL 941 ™, B. F. Goodrich Chemical company) | 0.05 |
| Sodium bisulfite | 0.01 |
| Ethyl p-hydroxybenzoate | 0.3 |
| Perfume | q.s. |
| Ion exchanged water | balance |

EXAMPLE 26 MILKY LOTION

The milky lotion was prepared by the following formula according to the same method as described in EXAMPLE 25.

| Stearic acid | 2.5 |
| --- | --- |
| Cetyl alcohol | 1.0 |
| Vaseline | 5.0 |
| Liquid paraffin | 10.0 |
| Polyoxyethylene (10) monooleate | 2.0 |
| Polyethylene glycol 1500 | 3.0 |
| Triethanolamine | 1.0 |
| 2-Hydroxy-3-methoxybenzoic acid | 5.0 |
| Glycyrrhizin acid | 0.5 |
| Amino acid | 0.3 |
| Carboxyvinyl polymer (CARBOPOL 941 ™, B. F. Goodrich Chemical company) | 0.05 |
| Sodium bisulfite | 0.01 |
| Ethyl p-hydroxybenzoate | 0.3 |
| Perfume | q.s. |
| Ion exchanged water | balance |

EXAMPLE 27 MILKY LOTION

The milky lotion was prepared by the following formula. Namely, the oil phase and the aqueous phase were prepared by dissolving the ingredients at 70° C., respectively. The oil phase was added in the aqueous phase, and emulsified by an emulsifier, and cooled down to 30° C. by using a heat exchange machine.

| [Oil phase] | |
| --- | --- |
| Stearyl alcohol | 2.0 |
| Squalene | 2.0 |
| Vaseline | 2.5 |
| Deodorized liquid lanolin | 1.5 |
| Evening primrose oil | 2.0 |
| Isopropyl myristate | 5.0 |
| Glyceryl monooleate | 2.0 |
| Polyoxyethylene (60) hydrogenated castor oil | 2.0 |
| Tocopherol acetate | 0.05 |
| 2-Hydroxy-5-buthoxybenzoic acid | 2.0 |
| Ethyl p-hydroxybenzoate | 0.2 |
| Butyl p-hydroxybenzoate | 0.1 |
| Perfume | q.s. |
| [Aqueous phase] | |
| Glycerin | 5.0 |
| Sodium hyaluronate | 0.01 |
| Carboxyvinyl polymer (CARBOPOL 941 ™, B. F. Goodrich Chemical company) | 0.2 |
| Potassium hydroxide | 0.2 |
| Sodium bisulfite | 0.01 |
| Ion exchanged water | balance |

EXAMPLE 28 MILKY LOTION

The milky lotion was prepared by the following formula according to the same method as described in EXAMPLE

27.

[Oil phase]

| | |
|---|---|
| Stearyl alcohol | 1.4 |
| Squalene | 2.0 |
| Vaseline | 2.5 |
| Deodorized liquid lanolin | 1.5 |
| Evening primrose oil | 2.0 |
| Isopropyl myristate | 5.5 |
| Glycerin monooleate | 2.0 |
| Polyoxyethylene (60) hydrogenated castor oil | 2.0 |
| Tocopherol acetate | 0.05 |
| 2-Hydroxy-4-butoxybenzoic acid | 1.5 |
| Ethyl p-hydroxybenzoate | 0.2 |
| Butyl p-hydroxybezoate | 0.1 |
| Perfume | q.s. |

[Aqueous phase]

| | |
|---|---|
| Glycerin | 5.0 |
| Sodium chondroitin sulfate | 0.01 |
| Carboxyvinyl polymer (CARBOPOL 941 ™, B. F. Goodrich Chemical company) | 0.2 |
| Potassium hydroxide | 0.2 |
| Citric acid | 0.01 |
| Sodium citrate | 0.1 |
| Ion exchanged water | balance |

EXAMPLE 29 JELLY

The jelly was prepared by the following formula. Namely, the carboxyvinyl polymer was uniformly dissolved in the ion exchanged water (Aqueous phase). The polyoxyethylene (50) oleyl ether was dissolved in the 95% ethanol and the system was added into the aqueous phase. The other ingredients were added to the system and sodium hydroxide and L-arginine were added for neutralizing and thickening.

[Formula]

| | |
|---|---|
| 95% Ethanol | 10.0 |
| Dipropylene glycol | 12.5 |
| Polyoxyethylene (50) oleyl ether | 2.0 |
| Carboxyvinyl polymer (CARBOPOL 941 ™, B. F. Goodrich Chemical company) | 1.0 |
| 2-Hydroxy-4-propoxy benzoic acid | 0.05 |
| Sodium hydroxide | 0.15 |
| L-arginine | 0.1 |
| Sodium 2-hydroxy-4-methoxybenzophenone sulfonate | 0.05 |
| Methyl p hydroxybenzoate | 0.2 |
| Trisodium ethylenediamine tetraacetate dehydrate | 0.05 |
| Perfume | q.s. |
| Ion exchanged water | balance |

EXAMPLE 30 SKIN LOTION

The skin lotion was prepared by the following formula. Namely, the A phase and C phase were uniformly dissolved, respectively. A phase was added to the C phase and the B phase was added to the system and dissolved.

[A phase]

| | |
|---|---|
| 95% Ethanol | 10.0 |
| Polyoxyethylene (20) octyldodecyl dodecanol | 1.1 |
| Methyl p-hydroxybenzoate | 0.2 |
| Pantotenyl ethyl ether | 0.1 |
| 2-hydroxy-4-methoxybenzoic acid | 0.05 |

[B PHASE]

| | |
|---|---|
| Potassium hydroxide | 0.1 |

[C PHASE]

| | |
|---|---|
| Glycerine | 5.0 |
| Dipropylene glycol | 10.0 |
| Sodium bisulfite | 0.03 |
| Carboxyvinyl polymer (CARBOPOL 941 ™, B. F. Goodrich Chemical company) | 0.2 |
| Purified water | balance |

EXAMPLE 31 PACK

The pack was prepared by the following formula. Namely the A phase. B phase and C phase were uniformly dissolved, respectively. The B phase was added to the A phase, and C phase was added to the system.

[A phase]

| | |
|---|---|
| Dipropylene glycol | 6.0 |
| Polyoxyethylene (60) hydrogenated castor oil | 5.0 |

[B phase]

| | |
|---|---|
| 2-hydroxy-3-methoxybenzoic acid | 1.3 |
| 2-hydroxy-4-methoxybenzoic acid | 1.5 |
| 2-hydroxy-5-methoxybenzoic acid | 0.7 |
| Olive oil | 5.0 |
| Tocopherol acetate | 0.2 |
| Ethyl p-hydroxybenzoate | 0.2 |
| Perfume | q.s. |

[C phase]

| | |
|---|---|
| Polyvinyl alcohol (saponification degree 90, polymerization degree 2,000) | 13.0 |
| Ethanol | 7.0 |
| Sodium bisulfite | 0.03 |
| Purified water | balance |

EXAMPLE 32 PACK INCLUDING POWDER

The pack including powder was prepared by the following formula. Namely the aqueous phase and alcohol phase were uniformly dissolved at room temperature, respectively. The alcohol phase was added to the aqueous phase, and mixed uniformly.

[Alcohol phase]

| | |
|---|---|
| 95% Ethanol | 10.0 |
| Propylene glycols | 5.0 |
| 2-Hydroxy-4-methoxybenzoic acid | 5.0 |
| 2-Hydroxy-4-ethoxybenzoic acid | 5.0 |
| Perfume | q.s. |
| Dye | q.s. |

[AQUEOUS PHASE]

| | |
|---|---|
| Zinc oxide | 25.0 |
| Kaolin | 20.0 |
| Glycerin | 5.0 |
| Methyl p-hydroxybenzoate | 0.2 |
| Ion exchanged water | balance |

EXAMPLE 33 CREAM

The cream was prepared by the following formula. Namely, the propylene glycol and potassium hydroxide were added to the ion exchanged water and kept at 70° C. (Aqueous phase). The other ingredients are mixed and dissolved at 70° C. (Oil phase). The oil phase was added to the aqueous phase gradually and preemulsified at 70° C., then uniformly emulsified with a homo mixer and cooled down to 30° C. under stirring condition.

| Stearic acid | 6.0 |
|---|---|
| Cetostearyl alcohol | 3.0 |
| Isopropyl myristate | 18.0 |
| Glycerine monostearate | 3.0 |
| Propylene glycol | 10.0 |
| 2-hydroxy-4-methylbenzoic acid | 15.0 |
| Potassium hydroxide | 0.2 |
| Sodium bisulfite | 0.01 |
| Preservatives | q.s. |
| Perfume | q.s |
| Ion exchanged water | balance |

EXAMPLE 34 CREAM

The cream was prepared by the following formula. Namely, propylene glycol was added to the ion exchanged water and kept at 70° C. (Aqueous phase). The other ingredients were mixed and dissolved at 70° C. (Oil phase). The oil phase was added to the aqueous phase gradually and preemulsified at 70° C., then uniformly emulsified with a homo mixer and then cooled down to 30° C. under stirring condition.

| Stearic acid | 5.0 |
|---|---|
| Sorbitan mono stearate | 2.5 |
| Polyoxyethylene (20) sorbitan monostearate | 1.5 |
| Propylene glycol | 10.0 |
| 2-hydroxy-3-ethylbenzoic acid | 3.0 |
| Glycerin trioctanoate | 10.0 |
| Squalene | 5.0 |
| Sodium bisulfite | 0.01 |
| Ethyl p-hydroxybenzoate | 0.3 |
| Perfume | q.s. |
| Ion exchanged water | balance |

EXAMPLE 35 CREAM

The cream was prepared by the following formula according to the same method as described in EXAMPLE 34.

| Stearyl alcohol | 7.5 |
|---|---|
| Stearic acid | 1.5 |
| Hydrogenated lanolin | 2.0 |
| Squalane | 5.0 |
| 2-Octadodecyl alcohol | 6.0 |
| Polyoxyethylene (25) cetyl ether | 3.0 |
| Glycerin monostearate | 2.0 |
| Propylene glycol | 5.0 |
| 2-hydroxy-4-propylbenzoic acid | 2.0 |
| Sodium bisulfite | 0.03 |
| Ethyl p-hydroxybenzoate | 0.3 |
| Perfume | q.s. |
| Ion exchanged water | balance |

EXAMPLE 36 CREAM

The cream was prepared by the following formula according to the same method as described in EXAMPLE 34.

| Stearic acid | 6.5 |
|---|---|
| Sorbitan monostearate | 2.0 |
| Polyoxyethylene (20) sorbitan monostearate | 1.5 |
| Propylene glycol | 10.0 |
| 2-hydroxy-5-methylbenzoic acid | 10.0 |
| Glycerin trioctanoate | 10.0 |
| Squalane | 5.0 |
| Sodium bisulfite | 0.03 |
| Ethyl p-hydroxybenzoate | 0.3 |
| Perfume | q.s. |
| Ion exchanged water | balance |

EXAMPLE 37 CREAM

The cream was prepared by the following formula according to the same method as described in EXAMPLE 34.

| Stearyl alcohol | 5.5 |
|---|---|
| Stearic acid | 2.5 |
| Hydrogenated lanolin | 2.0 |
| Squalane | 5.0 |
| 2-Octyl dodecylalcohol | 6.0 |
| Polyoxyethylene (25) cetyl ether | 3.0 |
| Glycerin monostearate | 2.0 |
| Propylene glycol | 5.0 |
| 2-hydroxy-3-methylbenzoic acid | 5.0 |
| Sodium bisulfite | 0.03 |
| Ethyl p-hydroxybenzoate | 0.3 |
| Perfume | q.s. |
| Ion exchanged water | balance |

EXAMPLE 38 CREAM

The cream was prepared by the following formula according to the same method as described in EXAMPLE 34.

| Stearyl alcohol | 5.0 |
|---|---|
| Stearic acid | 2.5 |
| Hydrogenated lanolin | 2.5 |
| Squalane | 5.0 |
| 2-Octyl dodecylalcohol | 6.0 |
| Polyoxyethylene (25) cetyl ether | 3.0 |
| Glycerin monostearate | 2.0 |
| Propylene glycol | 7.0 |
| 2-hydroxy-4-ethylbenzoic acid | 0.5 |
| Sodium bisulfite | 0.03 |
| Ethyl p-hydroxybenzoate | 0.3 |
| Perfume | q.s. |
| Ion exchanged water | balance |

EXAMPLE 39 CREAM

The cream was prepared by the following formula according to the same method as described in EXAMPLE 34.

| Stearyl alcohol | 6.0 |
|---|---|
| Stearic acid | 3.0 |
| Hydrogenated lanolin | 2.0 |
| Squalane | 5.0 |
| 2-Octyl dodecylalcohol | 6.0 |
| Polyoxyethylene (25) cetyl ether | 3.0 |
| Glycerin monostearate | 2.0 |
| Propylene glycol | 5.0 |
| 2-hydroxy-4-isobutylbenzoate | 0.05 |
| Sodium bisulfite | 0.03 |
| Ethyl p-hydroxybenzoate | 0.3 |
| Perfume | q.s. |
| Ion exchanged water | balance |

EXAMPLE 40 MILKY LOTION

The milky lotion was prepared by the following formula. Namely, the carboxyvinyl polymer was dissolved in a part of the ion exchanged water (A phase). The polyethylene glycol 1500 and the triethanolamine were added to the other part of ion exchanged water and dissolved at 70° C. (Water phase). The other ingredients were dissolved under heating condition at 70° C. (Oil phase). The oil phase was added to the aqueous phase and preemulsified. The A phase was added to the system and emulsified uniformly with the Homo mixer and cooled down to 30° C. under stirring condition.

| | |
|---|---|
| Stearic acid | 2.0 |
| Cetyl alcohol | 1.5 |
| Vaseline | 5.0 |
| Liquid paraffin | 10.0 |
| Polyoxyethylene (10) monooleate ester | 2.0 |
| Polyethylene glycol 1500 | 3.0 |
| Triethanolamine | 1.0 |
| 2-Hydroxy-3-methylbenzoic acid | 2.0 |
| Carboxyvinyl polymer (CARBOPOL 941 ™, B. F. Goodrich Chemical company) | 0.05 |
| Sodium bisulfite | 0.01 |
| Ethyl p-hydroxybenzoate | 0.3 |
| Perfume | q.s. |
| Ion exchanged water | balance |

EXAMPLE 41 MILKY LOTION

The milky lotion was prepared by the following formula according to the same method as described in EXAMPLE 40.

| | |
|---|---|
| Stearic acid | 2.5 |
| Cetyl alcohol | 1.0 |
| Vaseline | 5.0 |
| Liquid paraffin | 10.0 |
| Polyoxyethylene (10) monooleate | 2.0 |
| Polyethylene glycol 1500 | 3.0 |
| Triethanolamine | 1.0 |
| 2-Hydroxy-4-methylbenzoic acid | 7.5 |
| Carboxyvinyl polymer (CARBOPOL 941 ™, (B. F. Goodrich Chemical company) | 0.05 |
| Sodium bisulfite | 0.01 |
| Ethyl p-hydroxybenzoate | 0.3 |
| Perfume | q.s. |
| Ion exchanged water | balance |

EXAMPLE 42 MILKY LOTION

The milky lotion was prepared by the following formula. Namely, the oil phase and the aqueous phase were prepared by dissolving the ingredients at 70° C. respectively. The oil phase was added in the aqueous phase, emulsified by an emulsifier, and cooled down to 30° C. by a heat exchange machine.

| | |
|---|---|
| [Oil phase] | |
| Stearyl alcohol | 2.0 |
| Squalene | 2.0 |
| Vaseline | 2.5 |
| Deodorized liquid lanoline | 1.5 |
| Evening primrose oil | 2.0 |
| Isopropyl myristate | 5.0 |
| Glycerin monooleate | 2.0 |
| Polyoxyethylene (60) hydrogenated castor oil | 2.0 |
| Tocopherol acetate | 0.05 |
| 2-Hydroxy-5-methylbenzoic acid | 3.0 |
| Ethyl p-hydroxybenzoate | 0.2 |
| Butyl p-hydroxybenzoate | 0.1 |
| Perfume | q.s. |
| [Aqueous phase] | |
| Glycerin | 5.0 |
| Sodium hyaluronate | 0.01 |
| Carboxyvinyl polymer (CARBOPOL 941 ™, B. F. Goodrich Chemical company) | 0.2 |
| Potassium hydroxide | 0.2 |
| Sodium bisulfite | 0.01 |
| Ion exchanged water | balance |

EXAMPLE 43 MILKY LOTION

The milky lotion was prepared by the following formula according to the same method as described in EXAMPLE 42.

| | |
|---|---|
| [Oil phase] | |
| Stearyl alcohol | 1.4 |
| Squalene | 2.0 |
| Vaseline | 2.5 |
| Deodorized liquid lanolin | 1.5 |
| Evening primrose oil | 2.0 |
| Isopropyl myristate | 5.5 |
| Glycerin monooleate | 2.0 |
| Polyoxyethylene (60) hydrogenated castor oil | 1.5 |
| Tocopherol acetate | 0.05 |
| 2-Hydroxy-4-butylbenzoic acid | 2.0 |
| Ethyl p-hydroxybenzoate | 0.2 |
| Butyl p-hydroxybenzoate | 0.1 |
| Perfume | q.s. |
| [Aqueous phase part] | |
| Glycerin | 5.0 |
| Sodium hyaluronate | 0.01 |
| Carboxyvinyl polymer (CARBOPOL 941 ™, B. F. Goodrich Chemical company) | 0.2 |
| Potassium hydroxide | 0.2 |
| Sodium bisulfite | 0.01 |
| Ion exchanged water | balance |

EXAMPLE 44 JELLY

The jelly was prepared by the following formula. Namely, the carboxyvinyl polymer was uniformly dissolved in the ion exchanged water (Aqueous phase) The polyoxyethylene (50 moles) oleyl ether was dissolved in the 95% ethanol and the system was added into the aqueous phase. The other ingredients were added to the system and sodium hydroxide and L-arginine were added for neutralizing and thickening.

| | |
|---|---|
| [Formula] | |
| 95% Ethanol | 10.0 |
| Dipropylene glycol | 12.5 |
| Polyoxyethylene (50) oleyl ether | 2.0 |
| Carboxyvinyl polymer (CARBOPOL 941 ™, B. F. Goodrich Chemical company) | 1.0 |
| 2-Hydroxy-4-propyl benzoic acid | 0.05 |
| Sodium hydroxide | 0.15 |
| L-arginine | 0.1 |
| Sodium 2-hydroxy-4-methoxybenzophenone sulfonate | 0.05 |
| Methyl p-hydroxybenzoate | 0.2 |
| Trisodium ethylenediamine tetraacetate dihydrate | 0.05 |
| Perfume | q.s. |
| Ion exchanged water | balance |

EXAMPLE 45 SKIN LOTION

The skin lotion was prepared by the following formula. Namely, the A phase and C phase were uniformly dissolved, respectively. The A phase was added to the C phase and the B phase was added to the system and dissolved.

| [A phase] | |
|---|---|
| 95% Ethanol | 10.0 |
| Polyoxyethylene (20) octyldodecyl dodecanol | 1.1 |
| Methyl p-hydroxybenzoate | 0.2 |
| Pantotenyl ethyl ether | 0.1 |
| 2-Hydroxy-4-methylbenzoic acid | 0.5 |
| [B PHASE] | |
| Potassium hydroxide | 0.1 |
| [C PHASE] | |
| Glycerine | 5.0 |
| Dipropylene glycol | 10.0 |
| Sodium bisulfite | 0.03 |
| Carboxyvinyl polymer (CARBOPOL 941 ™, B. F. Goodrich Chemical company) | 0.2 |
| Purified water | balance |

EXAMPLE 46 PACK

The pack was prepared by the following formula. Namely the A phase, B phase and C phase were uniformly dissolved respectively. The B phase was added to the A phase, and C phase was added to the system.

| [A phase] | |
|---|---|
| Dipropylene glycol | 6.0 |
| Polyoxyethylene (60) hydrogenated castor oil | 5.0 |
| [B phase] | |
| 2-hydroxy-3-methylbenzoic acid | 0.5 |
| 2-hydroxy-4-methylbenzoic acid | 1.5 |
| 2-hydroxy-5-methylbenzoic acid | 1.5 |
| Olive oil | 5.0 |
| Tocopherol acetate | 0.2 |
| Ethyl p-hydroxybenzoate | 0.2 |
| Perfume | q.s. |
| [C phase] | |
| polyvinyl alcohol (saponification degree 90, polymerization degree 2,000) | 13.0 |
| Ethanol | |
| Sodium bisulfite | |
| Purified water | balance |

EXAMPLE 47 PACK INCLUDING POWDER

The pack including powder was prepared by the following formula. Namely the aqueous phase and alcohol phase were uniformly dissolved at room temperature, respectively. The alcohol phase was added to the aqueous phase and mixed uniformly.

| [Alcohol phase] | |
|---|---|
| 95% Ethanol | 10.0 |
| Propylene glycol | 2.5 |
| 2-Hydroxy-5-ethylbenzoic acid | 5.0 |
| 2-Hydroxy-4-propylbenzoic acid | 7.5 |
| Perfume | q.s. |
| Dye | q.s. |
| [ALCOHOL PHASE] | |
| Zinc oxide | 25.0 |
| Kaolin | 20.0 |
| Glycerin | 5.0 |
| Methyl p-hydroxybenzoate | 0.3 |
| Ion exchanged water | balance |

The 2-hydroxy alkoxy benzoic acid derivatives included in the external preparation for the skin according to the present invention have suppression effect of melanine generation by inhibition of tyrosinase activity. Accordingly, excellent bleaching effect based on the suppression of chromatosis and high safety can be obtained.

The bleaching effect can be improved by adding acid mucopolysaccharide, vitamin E ester, p-hydroxybenzoate ester or alkylene diamine carboxylate derivative into the external preparation for the skin.

The 2-hydroxy alkylbenzoic acid derivatives included in the external preparation for the skin according to the present invention have also suppression effect of melanine generation by inhibition of tyrosinase activity. Accordingly, excellent bleaching effect based on suppression of chromatosis and high safety can be obtained.

What is claimed is:

1. An external preparation for the skin comprising a 2-hydroxy benzoic acid derivative and/or salt thereof in an amount sufficient to achieve a bleaching effect, represented by the following formula:

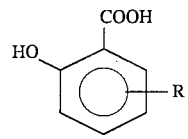

wherein R is an alkoxy group having 1–4 carbon atoms, and wherein said external preparation is a lotion, a cream, a cosmetic, a pack, a jelly, or an ointment.

2. An external preparation for the skin according to claim 1, wherein said alkoxy group is methoxy group.

3. An external preparation for the skin according to claim 1, wherein said alkoxy group is ethoxy group.

4. An external preparation for the skin according to claim 1, further comprising acid mucoplysaccharides selected from the group consisting of sodium hyaluronate and sodium chondroitinsulfate in a range from 0.01% to 10% by weight.

5. An external preparation for the skin according to claim 1, further comprising vitamin E esters selected from the group consisting of α-tocopherol, β-tocopherol, γ-tocopherol, δ-tocopherol, tocopherol acetate and tocopherol nicotinate in a range from 0.01% to 3% by weight.

6. An external preparation for the skin according to claim 1, further comprising p-hydroxybenzoate derivatives selected from the group consisting of methyl p-hydroxybenzoate, ethyl p-hydroxybenzoate and butyl p-hydroxybenzoate in a range from 0.01% to 3% by weight.

7. An external preparation for the skin according to claim 1, further comprising ethylenediamine tetra acetic acid and salts thereof in a range from 0.01% to 3% by weight.

8. An external preparation for the skin according to claim 1, wherein said amount is in a range from 0.001% to 20% by weight.

9. An external preparation for the skin according to claim 1, wherein said amount is in a range from 0.01% to 10% by weight.

10. An external preparation for the skin according to claim 1, wherein said external preparation system is a solubilized system, an emulsified system or a dispersed system.

* * * * *